United States Patent [19]

Keane et al.

[11] Patent Number: 5,754,283
[45] Date of Patent: May 19, 1998

[54] COLOR MEASURING DEVICE HAVING INTERCHANGEABLE OPTICAL GEOMETRIES

[75] Inventors: Thomas J. Keane; Richard A. Cook, both of Gaithersburg., Md.

[73] Assignee: BYK-Gardner USA, Division of Atlana, Columbia, Md.

[21] Appl. No.: 512,630

[22] Filed: Aug. 8, 1995

Related U.S. Application Data

[63] Continuation-in-part of Ser. No. 329,280, Oct. 26, 1994, abandoned.

[51] Int. Cl.[6] .................... G01J 3/51; G01N 21/47; G01N 21/55
[52] U.S. Cl. ................. 356/73; 356/402; 356/445; 356/446
[58] Field of Search ................ 356/73, 402, 445, 356/446, 328

[56] References Cited

U.S. PATENT DOCUMENTS

| | | |
|---|---|---|
| 4,753,530 | 6/1988 | Knight et al. .................. 356/73 |
| 4,916,309 | 4/1990 | Keane ..................... 250/227.29 |
| 4,995,727 | 2/1991 | Kawagoe et al. ............... 356/402 |
| 5,168,320 | 12/1992 | Lutz et al. ................... 356/402 X |
| 5,196,906 | 3/1993 | Stover et al. .................. 356/446 |
| 5,319,437 | 6/1994 | Van Aken et al. ............... 356/326 |

*Primary Examiner*—Vincent P. McGraw
*Attorney, Agent, or Firm*—Ohlandt, Greeley, Ruggiero & Perle

[57] ABSTRACT

There is provided a high precision device for measuring the color of non-self-luminous or self-luminous objects having interchangeable optical geometries for conversion from one optical geometry to another. The device interchanges a plurality of modules, each having at least one optical geometry for directing illumination from an illumination source and for collecting sample light reflected from a measured object or sample. Such optical geometries include a 45/0 geometry, sphere geometry, specular included geometry, and specular excluded geometry. Each module is removably attached to the device when measurement of the color of the sample is desired and may be separated from the device when measurement of the color of the sample is not desired. Also, each module may include removable filters for absorbing certain types of light, such as ultraviolet visible light, and blocking elements to determine the source of any reference signal. The device may further include a sensing system that automatically determines which module has been installed and to appropriately configure the device.

17 Claims, 9 Drawing Sheets

COLOR MEASURING DEVICE HAVING INTERCHANGEABLE OPTICAL GEOMETRIES

RELATED APPLICATION

This application is a continuation-in-part of U.S. patent application Ser. No. 08/329,280, which was filed on Oct. 26, 1994, now abandoned and which application is incorporated by reference.

BACKGROUND OF THE INVENTION

I. Field of the Invention

The present invention relates generally to signal measuring devices or instruments, such as photometers, colorimeters, spectrophotometers, spectrocolorimeters and radiometers, for measuring the color of objects. More particularly, the present invention relates to a single color measuring device for measuring object color based on a wide variety of different optical geometries. The device has an adaptable lower end for interchangeably receiving any one of a plurality of interface modules, each module having the same or a different optical geometry.

An instrument that measures the color of an object must provide quantitative results in close conformance with the human observer's perception of the color of that object. The instrument must "see" an object in the same way that a person would see the object, without alteration. Since color is an aspect of the appearance of an object, the appearance of the object must not be altered in the color measurement process.

An object to be measured may have a limitless variety of shapes, forms, sizes and arrangements. Thus, a color measuring device must interface with the object so that it does not alter the appearance of the object and, thus, allows precise measurement. This has led to the development of different optical geometries for those different measuring needs.

As stated above, color is an aspect of the appearance of an object. For real objects, as opposed to pure radiated energy, the surface of the object is an important factor. For example, for two objects that are made from the same plastic resin and are identical in shape, size and other physical properties, one object has a polished surface and the other object has a matte finish. Both are made with the same colorants, however they will look very different in color. Another example, consider the appearance of a newly waxed surface as opposed to one that is dull and oxidized. At times, it is desired to measure an object's color in terms of how the eye sees it. At other times, it is desired to measure the color of an object to determine if two objects dissimilar in appearance are indeed made with the same colorants. This has lead to the development of different optical geometries for these different measuring needs.

The present invention is a color measuring device for adapting to the unique shape or characteristics of an object or sample and for other measurement needs by interchanging interface modules as necessary instead of requiring a multiplicity of instruments, each with a different geometry.

II. Description of the Prior Art

Color measuring devices, such as spectrophotometers, that illuminate samples to be measured using a single preset geometry are known. Such geometries include, but are not limited to, a 45/0 or 0/45 geometry and a sphere geometry, such as a d/0 geometry, d/8 geometry, 0/d geometry and 8/d geometry. For example, U.S. Pat. No. 5,319,437 to H. Van Aken, et al. titled HANDHELD PORTABLE SPECTROPHOTOMETER provides a spectrophotometer that illuminates a sample at an angle of 45° and receives a portion of the light reflected from the sample an angle of 0°. Thus, the spectrophotometer uses a 45/0 geometry to measure object color. To illuminate the sample using a different geometry, another separate spectrophotometer having different geometry is required. Thus, a user would need at least two spectrophotometers.

Typically, only one geometry is implemented when manufacturing a single color measuring device. Therefore, there is a need for a single color measuring device that can be adapted to convert from one optical geometry to another by way of a simple and inexpensive attachment. Such a device would permit a user to readily and easily perform the conversion from one optical geometry to another and permit measurement of various types of light, such as visible light, ultraviolet light, near-infrared and infrared light.

In addition, there is a need for an easy and inexpensive replacement of optical geometries that have deteriorated over time. For example, sphere geometries are generally coated internally with a highly reflecting flat white paint. The purpose of the coating is to achieve a high level of diffuse reflectivity that is required for such a color measuring device to work properly and efficiently. However, such coatings deteriorate over time leading to reduced sensitivity and poor performance and, further, the added expense and loss of time to repair or replace the entire color measuring device.

SUMMARY OF THE INVENTION

Against the foregoing background, it is a primary object of the present invention to provide a color measuring device having a single unit design and, yet, one that can handle a wide variety of coloring measurement tasks that require more than one optical geometry.

It is another object of the present invention to provide such a color measuring device with a plurality of simple and inexpensive attachments or modules, each having a particular optical or illuminating geometry, that may be attached to the device for conversion from one geometry to another or for repair/replacement of a deteriorated module.

It is a further object of the present invention to provide such a color measuring device in to which each module has recesses to receive filters that aid the device in identifying the presence or absence of brightening agents, such as phosphors, in measured objects or samples.

It is a still further object of the present invention to provide such a color measuring device with custom interface modules that are designed for special applications, such as color measurement of a sample that is difficult or impossible to measure with conventional, less flexible color measuring devices.

It is still another object of the present invention to provide such a color measuring device with an automatic sensing system that determines which module has been installed and configures the color measuring device accordingly.

To accomplish the foregoing objects and advantages, the present invention, in brief summary, is a device for measuring color of a sample which device has interchangeable optical geometries. The device comprises means for illuminating the sample; modular means, optically connected to the illuminating means, for directing at least a portion of the illumination to the sample and for collecting at least a portion of a sample light reflected from the sample; and means, optically connected to the modular means, for receiving the sample light from the modular means. The modular means has at least one optical geometry for determining the distribution of the illumination and the collection of the sample light by the modular means. Also, the modular means is optically separable from the illuminating means and the receiving means when measurement of the color of the sample is not being performed.

BRIEF DESCRIPTION OF THE DRAWINGS

The foregoing, and still further, objects and advantages of the present invention will be more apparent from the following detailed explanation of the preferred embodiments of the invention in connection with the accompanying drawings.

DETAILED DESCRIPTION OF THE PREFERRED EMBODIMENT

Figure 1:
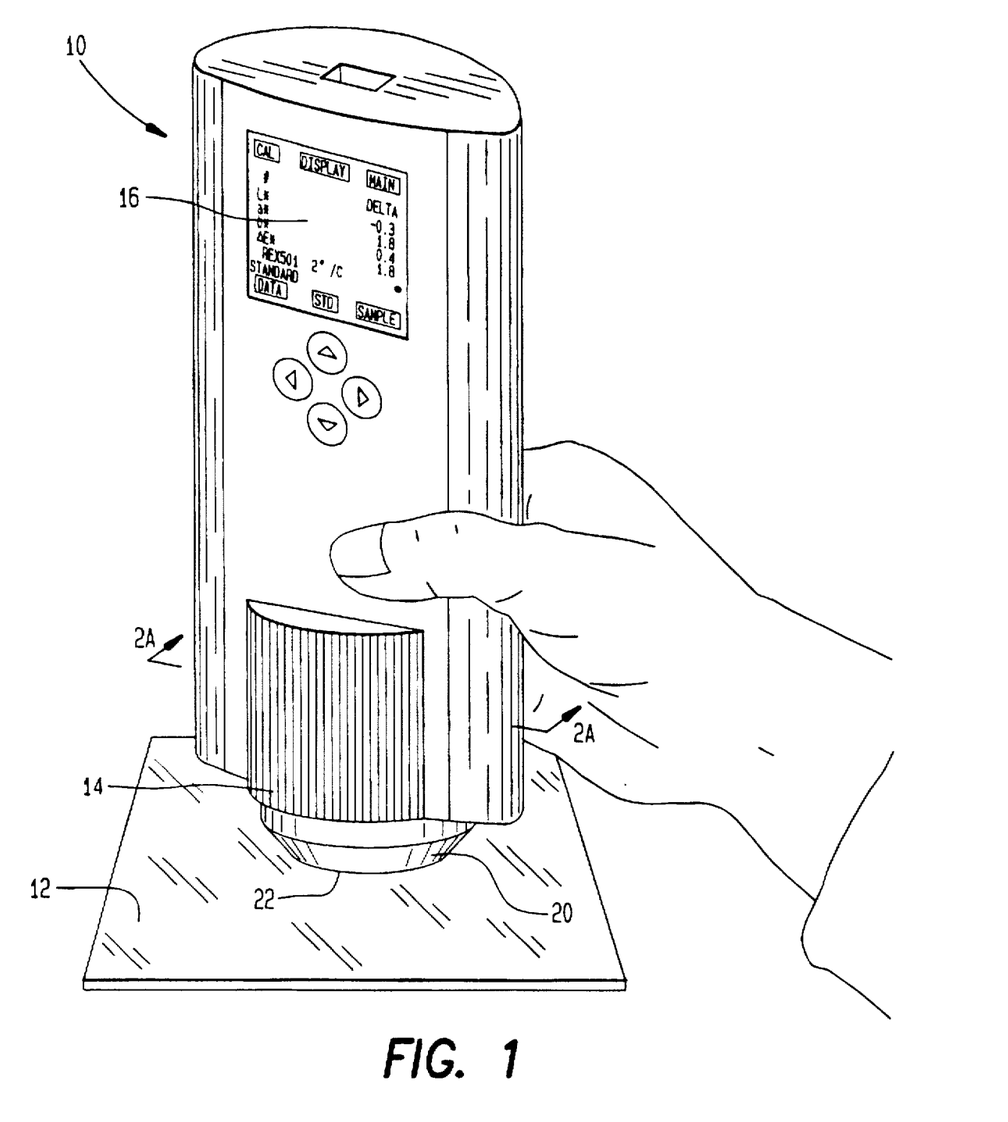
FIG. 1 is a perspective view of the preferred embodiment of the present invention.

Referring to the drawings and, in particular, to FIG. 1, there is provided a high precision color measuring device which is generally represented by reference numeral 10. It is to be understood that the present invention may be applied to a wide-variety of signal measuring devices or color measuring devices, such as photometers, spectrophotometers, colorimeters, spectrocolorimeters, radiometers and spectroradiometers, and is not restricted to device 10 shown in the drawings. The device 10 of the present invention is a high precision instrument for the measurement of object color of non-self-luminous objects, such as a flat surface or sample 12 as shown in FIG. 1. It is preferable that the device 10 be hand-held, however it may be incorporated into other apparatuses, such as bench-type apparatuses. The device 10 may be held horizontally, vertically or in angular position, provided its lower end 14 is close enough to the sample or object 12 to measure its color.

For the preferred embodiment of the present invention, as shown in FIG. 1, a removable nose cone or interface module 20 is attached to the lower portion 14 of the device 10 and situated vertically above and substantially adjacent to the sample 12 that is to be measured. The interface module 20 is attached to the lower end 14 of color measuring device 10 by any means that provides a secure optical and mechanical connection between the interface module and the device during operation while permitting, if desired, a user to easily detach and optically disconnect the interface module from the device. For the preferred embodiment, the interface module 20 is attached by an insert-and-twist locking mechanism, much like a bayonet-type connection.

A variety of different interface modules 20 may be attached and removed to change the optical geometry of the device 10. Such interface modules 20 may have a 45/0 geometry or a sphere geometry, such as d/0, d/8, 0/d and 8/d sphere geometries. Also, each sphere geometry may make measurements including specular illumination (SPIN) or excluding specular illumination (SPEX). Further, an interface module 20 may also be used to determine the size of the viewed area of the sample 12 that is viewed by the interface module. Some applications require a large viewing area for accurate color measurement of the sample 12, whereas other applications require a small viewing area.

Each interface module 20 includes the necessary optics and mechanical elements to provide a particular optical geometry, as described above, and accommodate different measuring conditions, including object variances of samples. Such object variances include size, shape, and texture, as well as color. Therefore, the interface module 20 positioned between the device 10 and the measured sample 12 is extremely important and must be capable of measuring object color without destroying or modifying the sample.

A color measurement of the sample 12 is made by the device 10, by positioning the lower surface 22 of the interface module 20 against or substantially adjacent to the sample and activating the device to measure the color of the sample. The device 10 is activated by pressing an Execute button on the rear side (not shown) of the device. The measured color, as well as the results of analytical calculations based on the measured color, will, subsequently, appear on a display or screen 16 on the front side of the device 10, such as a liquid crystal display. Alternatively, signals may be sent to an external host computer for further processing of these signals. Also, command signals may be received or data transferred to the device from an external host computer.

Figure 2A:
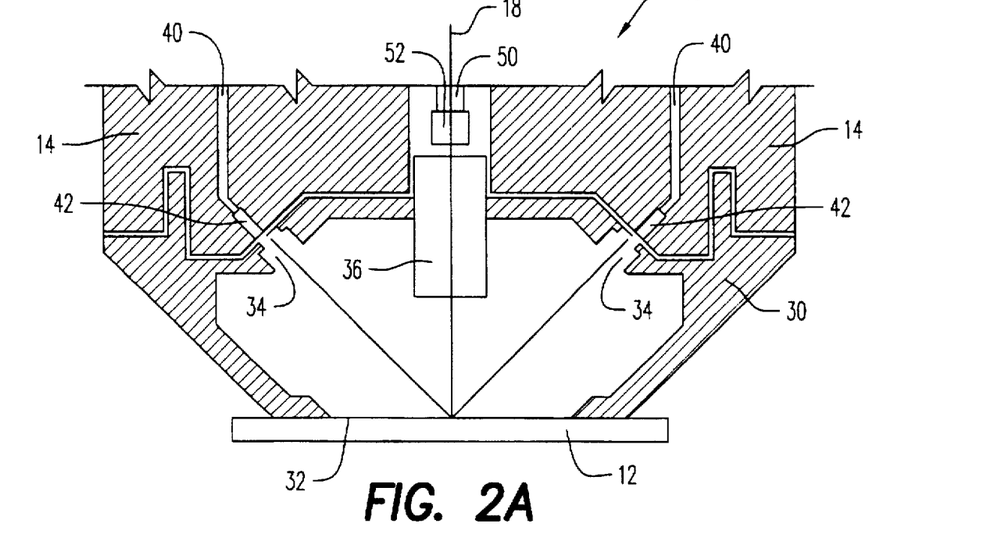
FIG. 2A is a sectional view taken along line 2A—2A of FIG. 1 of the interface module at the lower portion of the preferred embodiment.
Figure 2B:
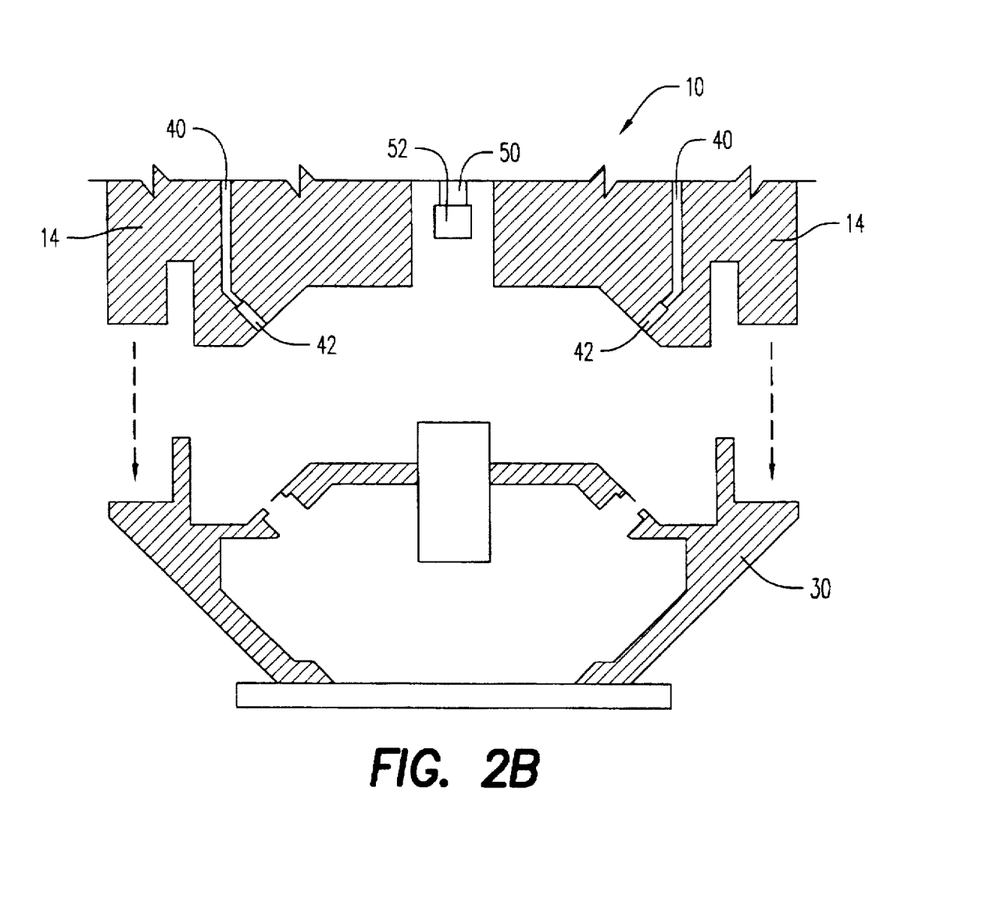
FIG. 2B is an exploded view of FIG. 2A in which the interface module has been separated from the lower end of the preferred embodiment.

FIGS. 2A and 2B show the modularity capability of the nose cone or interface module 20 of FIG. 1. As shown in FIG. 2A, a 45/0 module 30, i.e., an interface module having a 45/0 geometry, is attached to the lower portion 14 of the device such that the contour of the contacting surfaces of the 45/0 module and the lower portion conform to each other.

Referring in particular to FIG. 2A, the 45/0 module 30 includes a viewing end 32 for adjacently receiving the sample 12 to be measured, a plurality of peripheral apertures 34 for accommodating the transmitting ends 42 of various fiber optic or illuminating lines 40, and a lens system having a central port 36 for collecting sample light reflected from the sample 12. The sample light collected by the central port 36 is received by the device at a receiving end 52 of a receiving line 50. The sample 12 is illuminated by the illuminating lines 40 at 45° angles from a vertical viewing axis 18 relative to the sample.

Referring to FIG. 2B, the 45/0 module 30 is optically separated and physically detached from the lower portion 14 of the device 10, including the illuminating line 40 and the receiving line 50, when color measurement of the sample is not being performed.

Figure 3:
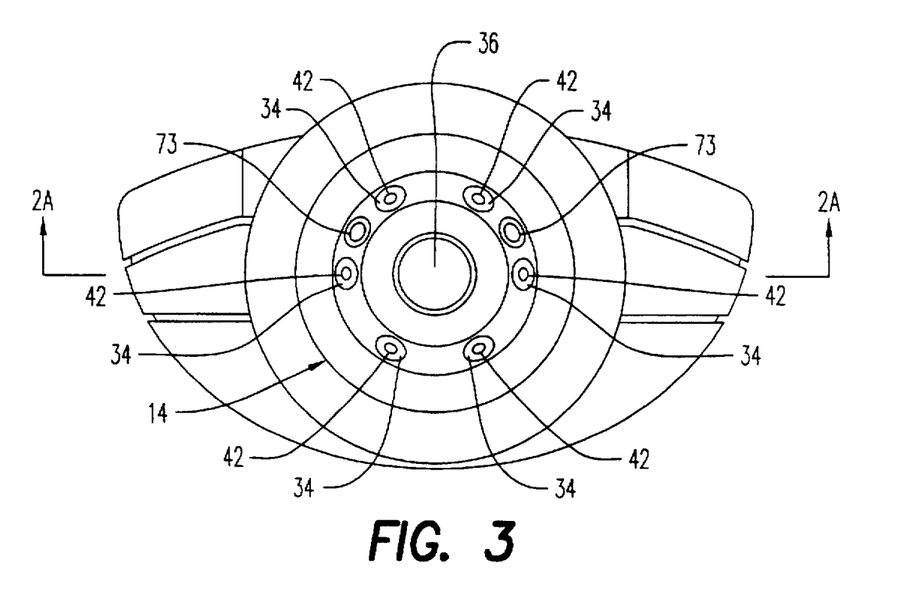
FIG. 3 is a bottom view of the preferred embodiment with the interface module removed.

Referring to FIG. 3, the transmitting ends 42 of the illuminating lines 40 may be situated at the lower end 14 of the color measuring device 10 in a variety of configurations. For example, the illumination from the illuminating lines 40 can be a single beam or multiple beams azimuthally separated or form a continuous ring of beams about the normal to the sample 12. For the preferred embodiment, the 45/0 module 30 has six peripheral apertures 34 situated equally apart in a ring formation about the sample 12, thus allowing six beams of illumination to illuminate the sample at 45° angles from the vertical viewing axis 18, as shown in FIGS. 2A and 3. Also shown in FIG. 3 are two receiving ends 73 of reference lines, described below, that may also be used for the present invention.

Figure 4:
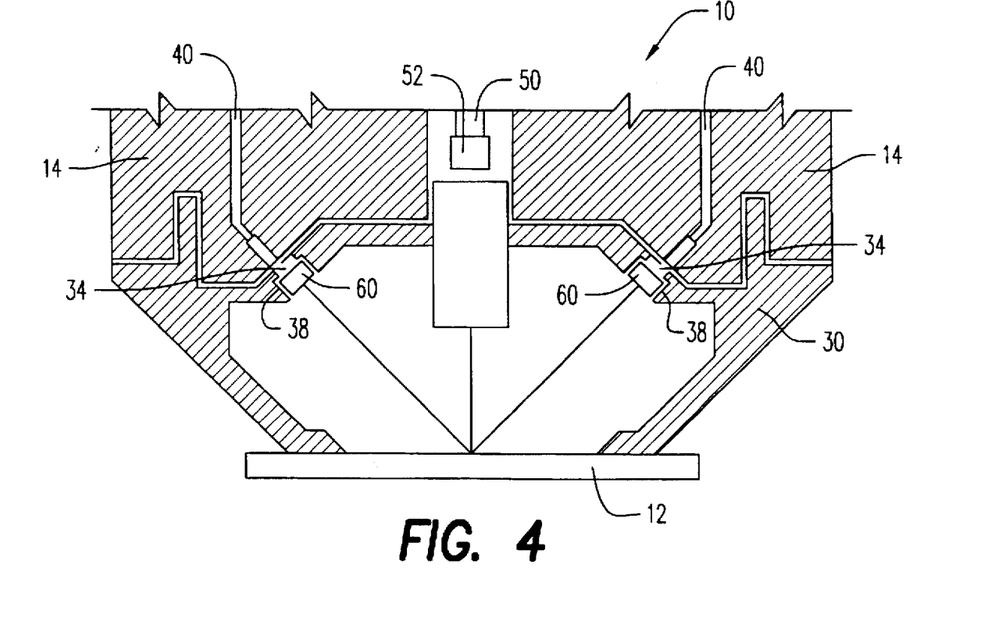
FIG. 4 is the sectional view of FIG. 2A in which the interface module includes two filter elements.

Referring to FIG. 4, the 45/0 module 30 includes removable filters 60 that are situated in a travel path of the illumination received from the illuminating line 40. Such filters 60 are used to determine the presence (and the amount) or absence of brightening agents or brighteners, such as phosphors, used in the samples 12. Since such brighteners often exhibit a fluorescence under a particular type of light, such as ultraviolet light, measurements taken with and without the filters 60 provide an indication of the presence or absence of brighteners used. The filters 60 are inserted within recesses 38 located adjacent to each peripheral aperture 34 of the 45/0 module 30. As stated above, the preferred embodiment has six peripheral apertures 34 and, thus, six filters 60 may be positioned within recesses 38 of the 45/0 module 30, two of which are shown in FIG. 4. Examples of the type of filters 60 that may be used include ultraviolet absorbing/visible transmitting filters, ultraviolet transmitting/visible absorbing filters, visible transmitting/infrared absorbing filters, infrared transmitting/visible blocking filters, selective absorption filters, and the like.

Figure 5:
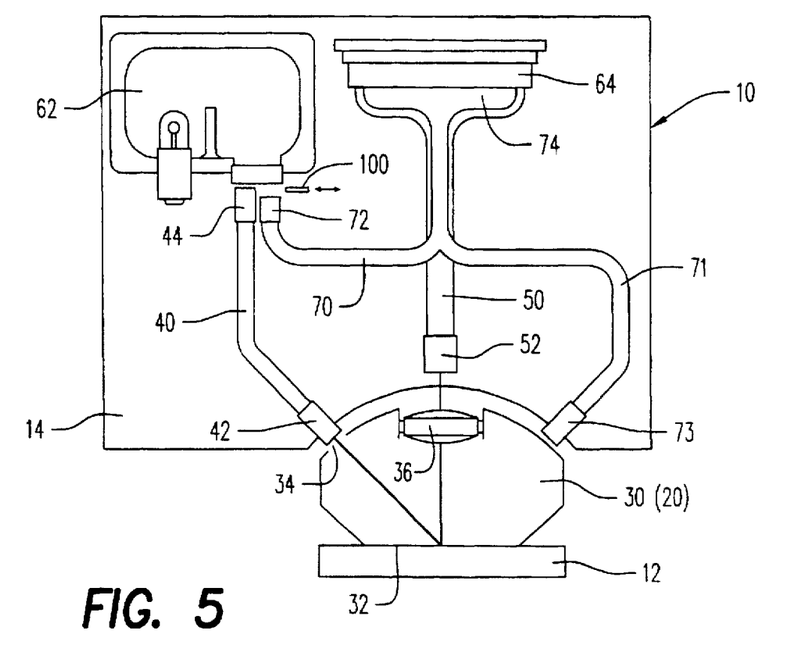
FIG. 5 is a diagrammatic view showing the basic internal components of the preferred embodiment of FIG. 1 with an interface module having a 45/0 geometry positioned at a lower end.
Figure 6:
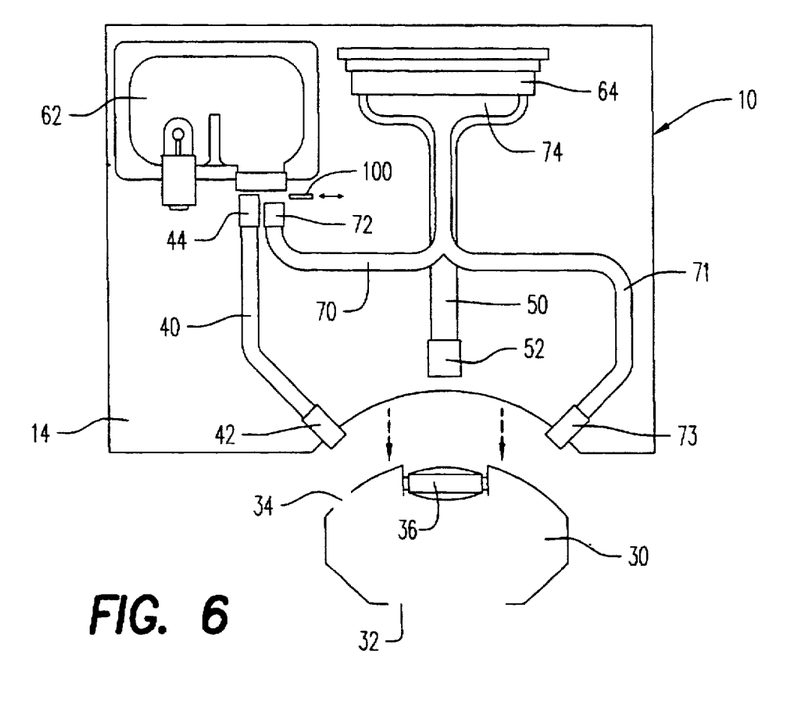
FIG. 6 is a diagrammatic view of the preferred embodiment of FIG. 5 with the interface module separated from the lower end of the preferred embodiment.

Referring to FIG. 5 and 6, there is shown a diagrammatic view of the basic internal components of the preferred embodiment with the 45/0 module 30 attached and separated, respectively, from the lower portion 14 of the color measuring device 10. For the preferred embodiment, a light source 62 is shown as a small integrating chamber having an incandescent light bulb. However, the type of light source 62 used in a spectrophotometer is unimportant provided it has sufficient energy for all desired wavelengths to be measured. For the 45/0 module 30, the light source 62 provides illumination to a receiving end 44 of the illuminating line 40 and a receiving end 72 of a first reference line 70. Also, a receiving end 73 of a second reference line 71, connect to the first reference line 70, is adapted to received reference light from the attached interface module 20, and a transmitting end 74 is connected to a separator/detector 64. Although the reference lines 70 and 71 are not essential for the operation of the present invention, they are provided in the present application by way of example.

Referring in particular to FIG. 5, the illuminating line 40 transmits the illumination received from the light source 62 to one of the apertures 34 of the 45/0 module 30. In this manner, the light source 62 and the illuminating line 40 produce illumination for illuminating the sample 12 that is positioned adjacent to the viewing end 32. Although only one aperture 34 is shown in FIG. 5, the preferred embodiment has a plurality of apertures, shown in FIG. 3, situated about the sample 12. The 45/0 module 30 directs a portion of the illumination to the sample 12 and collects the sample light that is reflected from the sample by the lens system through the central port 36. After passing through the central port 36, the receiving line 50 transmits the sample light to the separator/detector 64 for color measurement determination and further analysis. Thus, on a simple scale, a continual light pattern passes through the 45/0 module 30 since the 45/0 module is optically connected to the lower portion 14 of the device 10, particularly the illuminating line 40 and the receiving line 50.

Figure 7:
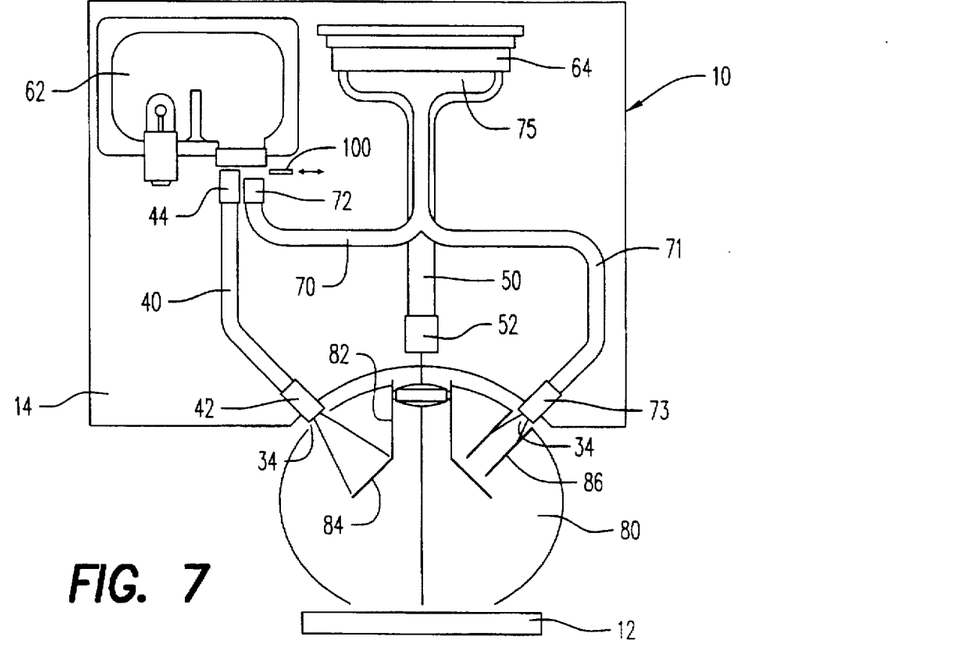
FIG. 7 is a diagrammatic view of the preferred embodiment of FIG. 1 with an interface module having a specular excluded (SPEX) d/0 sphere geometry.
Figure 8:
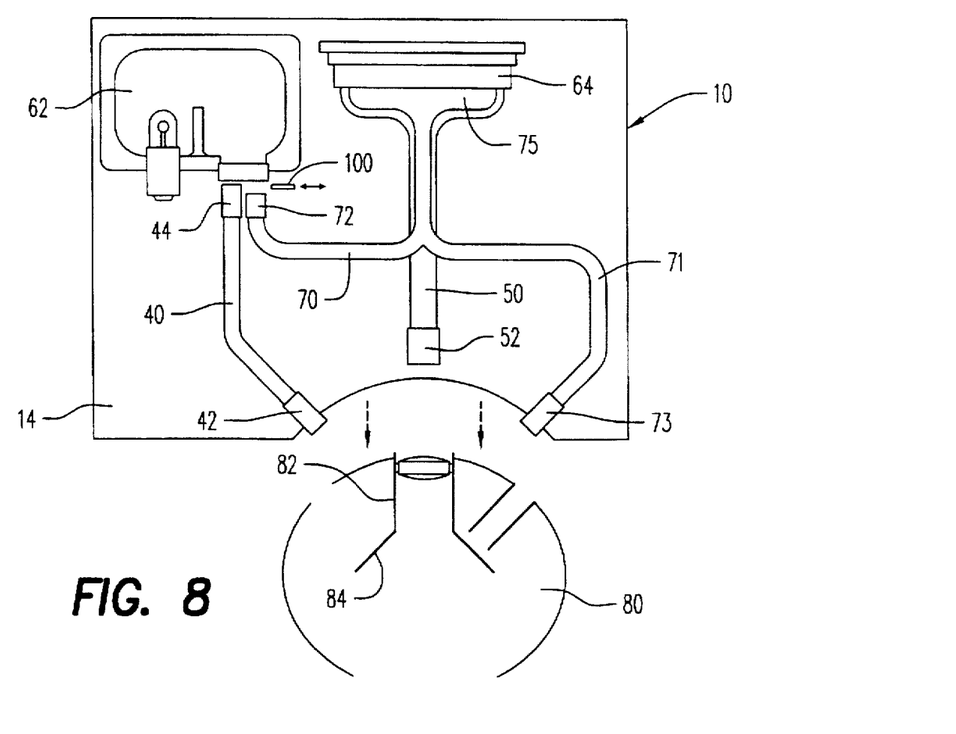
FIG. 8 is a diagrammatic view of the preferred embodiment of FIG. 7 with the interface module separated from the lower end of the preferred embodiment.

Referring to FIGS. 7 and 8, there is shown the preferred embodiment with a d/0 specular excluded sphere module or d/0 SPEX module 80. The d/0 SPEX module 80 includes a vertical cylindrical body 82 with outwardly flared end or partial cone portion 84. As with any typical sphere geometry, the interior surface of the d/0 SPEX module 80 is coated with a special white, reflective paint. However, the interior surface of the cylindrical body 82 and the cone portion 84 are coated with a highly absorbing black material to absorb specularly reflected light. The exterior surfaces of the cylindrical body 82 and the cone portion 84 are coated with the special white, reflective paint. Alternatively, the device may be fabricated of a bright, white material. The cylindrical body 82 and the cone portion 84 of the d/0 SPEX module are provided to prevent the illuminating lines 40 from directly illuminating the sample 12. In addition, a smaller cylindrical body 86 is positioned at the peripheral aperture 34 that receives the receiving end 73 of the second reference line 71. This smaller cylindrical body 86 prevents the second reference line 71 from directly viewing the sample 12 and the illumination emitted by the illuminating line 40.

Figure 9:
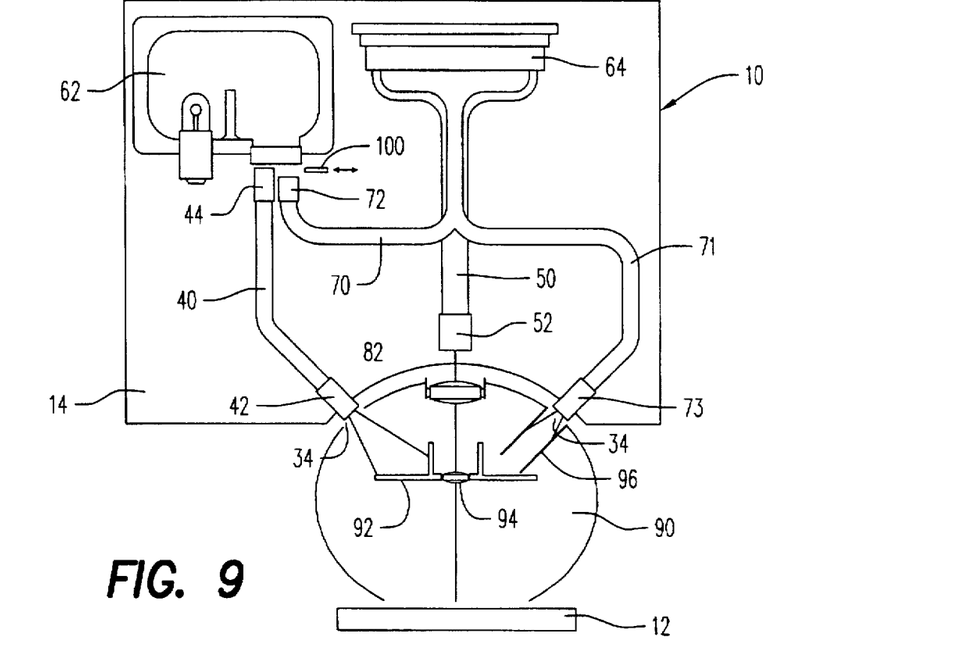
FIG. 9 is a diagrammatic view of preferred embodiment of FIG. 1 with an interface module having a specular included (SPIN) d/0 sphere geometry.
Figure 10:
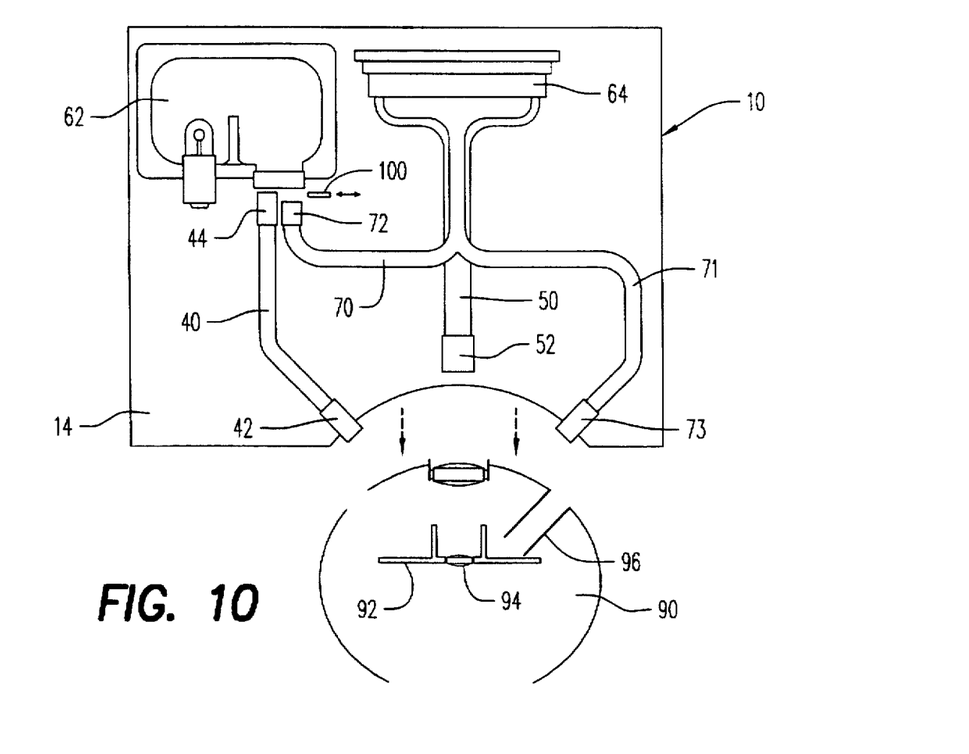
FIG. 10 is a diagrammatic view of FIG. 9 with the interface module separated from the lower end of the preferred embodiment.

Referring to FIGS. 9 and 10, there is shown the preferred embodiment with a d/0 specular included sphere module or d/0 SPIN module 90. The d/0 SPIN module 90 includes a device 92 in the middle of the module that is coated with a special white, reflective coating or paint, just like the interior surface of the module. This purpose of the special white, reflective paint is similar to that of the cone portion 84 of the d/0 SPEX module 80 of FIGS. 7 and 8. Also, like the d/0 SPEX module 80, the device may be fabricated of a bright, white material. However, the device 92 includes a lens 94 for collecting both diffusely and specularly reflective light from the d/0 SPIN module 90. Various lens arrangements provide for different areas of illumination and view. The cylinder 96 at the second reference line 71 serves the same purpose as in the d/0 SPEX module 80 of FIGS. 7 and 8. The substantially planar device 92 serves to block the illuminating light from directly illuminating the sample 12.

The color measuring device 10 of the preferred embodiment, shown in FIGS. 5 through 10, has been adapted to accommodate dual beam systems. In particular, the preferred embodiment includes a first reference line 70 that transmits reference light directly from the light source 62 to the separator/detector 64, whereas a second reference line 71 transmits reference light reflected from the sphere wall to the separator/detector. The preferred embodiment also includes a light blocking element 100 that is located adjacent to the receiving end 72 of the first reference line 70. Such a dual beam system is generally described in the above-identified pending U.S. patent application Ser. No. 08/329,280. Although a dual beam system may benefit from the features and advantages of the present invention, as described below, it is understood that the present invention has application to color measuring devices in general and is not restricted to a dual beam system.

In comparing the 45/0 module 30 of FIGS. 5 and 6 versus the modules having sphere geometries of FIGS. 7 through 10, the position of the light blocking element 100 relative to the receiving end 72 of the first reference line 70 is different. Since a dual beam system typically requires only one reference line to be active, i.e., to transmit reference light, at any given time, the light blocking element 100 prevents reference light from passing through the first reference line 70 when a reference light is transmitted through the second reference line 71. For example, as shown in FIGS. 7 and 9, light blocking element 100 prevents the receiving end 72 of the first reference line 70 from receiving a reference light since the d/0 SPEX module 80 or d/0 SPIN module 90 attached to the lower portion 14 requires a reference light from the interface module. On the other hand, the light blocking element 100 allows the receiving end 72 of the first reference line 70 to receive a reference light from the light source 62 for the 45/0 module 30 shown in FIG. 5. Blocking of the receiving end 73 of the second reference line 71 is not necessary for the preferred embodiment since the peripheral aperture 34 has been omitted from the 45/0 module.

Accordingly, in FIGS. 5 and 6, the reference light may be obtained from the light source 62 for the 45/0 module 30. In contrast, for the modules having sphere geometries shown in FIGS. 7 through 10, the reference light is obtained from the interface module to allow the system to correct for sphere efficiency changes and sphere discoloration, due to placement of the sample 12 at the viewing end 32. The preferred embodiment of the present invention is capable of changing the position of light blocking element 100, thus changing the source of the reference light, depending upon the type of interface module that is attached to the lower portion 14.

In addition to the reference blocking scheme shown in FIGS. 5 through 10, other means can be employed to achieve the same effect. In particular, it is important to use a scheme that allows only the appropriate illuminating and/or reference beam to be active at any given time as required by a particular interface module. Thus, the activity of the illuminating and reference beams may handled by other components of the color measuring device, such as the interface module 20, and is not restricted to the light blocking element 100 shown in FIGS. 5 through 10. Examples of such alternative schemes are shown in FIGS. 11 and 12.

Figure 11:
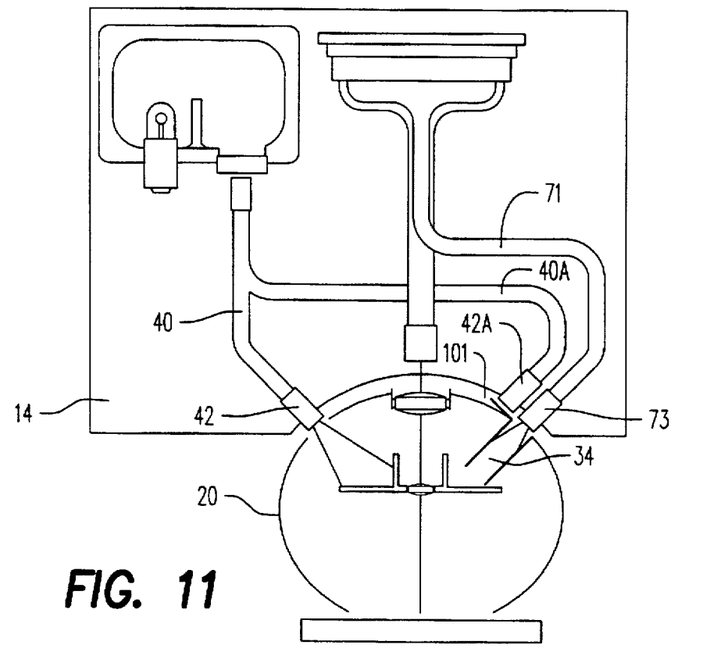
FIG. 11 is a diagrammatic view of the preferred embodiment of FIG. 1 with one end of an illuminating line blocked by an outer portion of the interface module.

Referring to FIG. 11, there is shown a scheme for blocking an illuminating light without the need for the dynamic light blocking element 100 shown in FIGS. 5 through and 10. Specifically, a light blocking portion 101 at the outer surface of the interface module 20 prevents illumination transmitted through the illuminating line 40A from entering into the interface module. When the interface module 20 is attached to the lower end 14 of the color measuring device 10, the transmitting end 42A of one or more illuminating lines 40 is aligned with the light blocking portion 101 of the interface module and the receiving end 73 of the reference line 71 is aligned with the peripheral aperture 34 of the interface module. Accordingly, illumination transmitted through the illuminating line 40A is blocked by light blocking portion 101.

Figure 12:
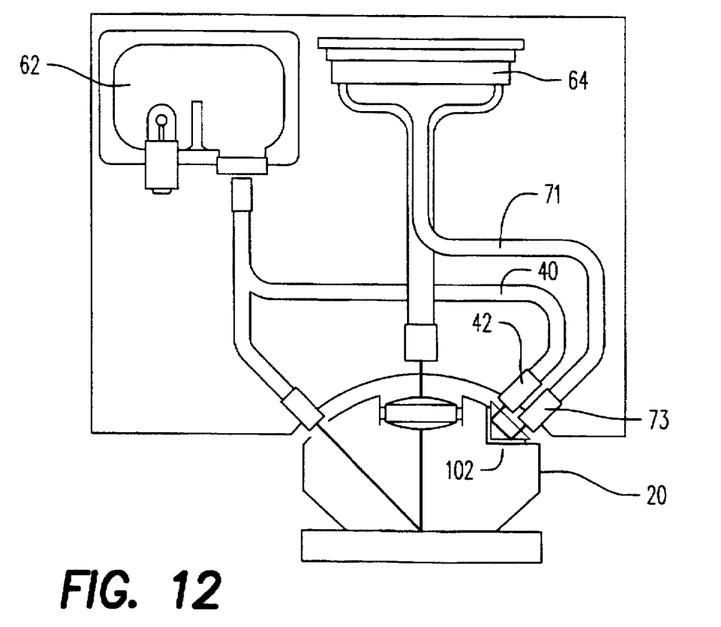
FIG. 12 is a diagrammatic view of the preferred embodiment of FIG. 1 in which illumination from a light source is re-directed to a separator/detector by a prism of the interface module.

Referring to FIG. 12, there is shown a scheme for transmitting illuminating light from the light source 62 to the interface module 20 and re-directs the illuminating light from the interface module to the separator/detector 64. The interface module 20 includes a prism 102 that is positioned in front of the transmitting end 42 of the illuminating line 40 and the receiving end 73 of the reference line 71. The prism 102 re-directs illumination received from the illuminating end 42 to the receiving end 43 and virtually allows the separator/detector 64 to view the light source 62 directly.

In addition to the 45/0 geometry and sphere geometries described above, a wide array of custom modules having unique geometries tailored to specific needs may be used with the device 10 of the present invention. Other types of custom interface modules are shown, by example, in FIGS. 13 through 15.

Figure 13:
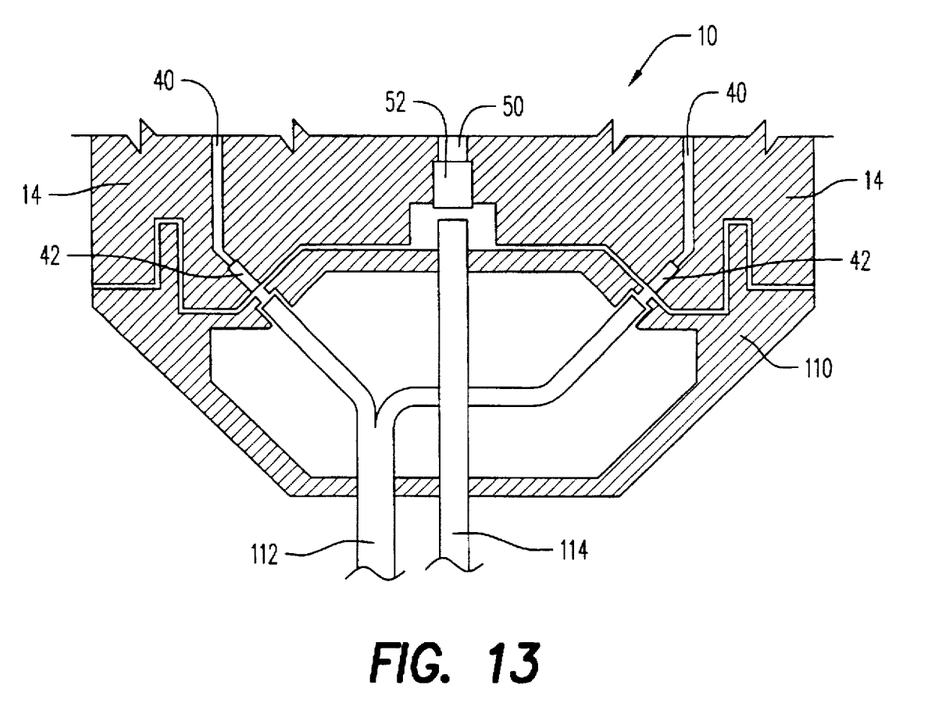
FIG. 13 is a sectional view of the preferred embodiment of FIG. 1 with an interface module having two extension lines leading to the outer environment of the interface module.

Referring to FIG. 13, there is shown a custom interface module 110 having a pair of flexible fiber optic cables or extension lines 112, 114 optically connected to the illuminating line 40 and the receiving line 50, respectively. Unlike the other interface modules 20, described above, the custom interface module 1 10 shown in FIG. 13 does not have an optical geometry setup within the module itself Instead the optical geometry of the custom interface module 110 is external to the module.

It is to be understood that the present invention may utilize a wide variety of methods and devices for aligning the ends of fiber optic cables for separable structures. For example, an alternative device for aligning fiber optic cables of an appliance and a separable probe is set forth in U.S. Pat. No. 4,916,309, which issued on Apr. 10, 1990, titled APPLIANCE FOR CONVERTING REFLECTANCE MEASURING INSTRUMENT INTO A TRANSMITTANCE MEASURING INSTRUMENT. U.S. Pat. No. 4,916,309 is owned by the assignee of the present invention and is incorporated herein by reference.

Figure 14:
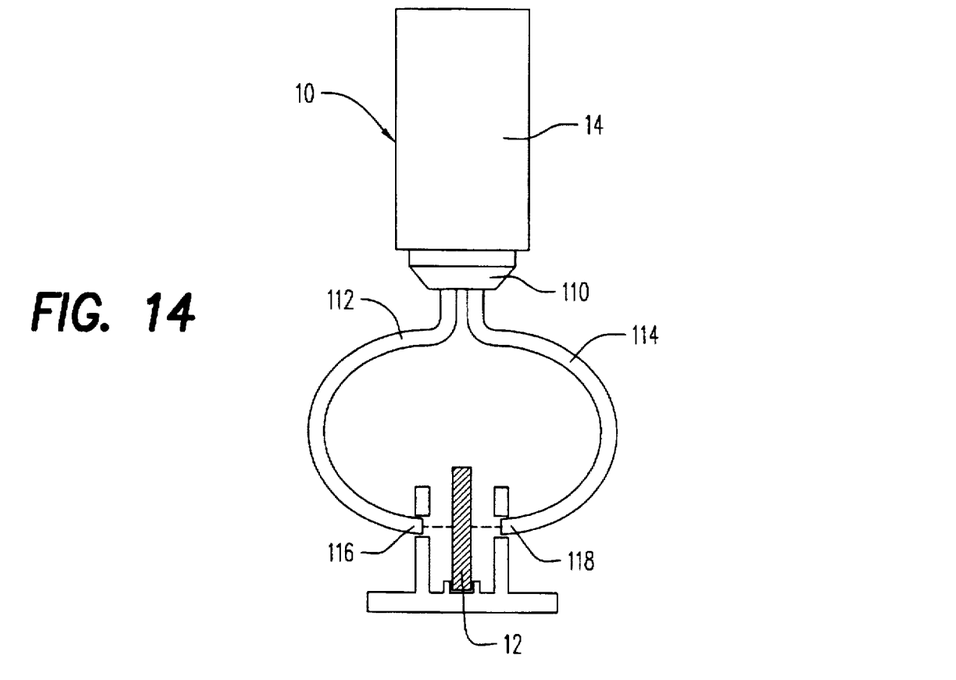
FIG. 14 is a side elevational view of the preferred embodiment of FIG. 1 with the interface module of FIG. 13 showing the two extension lines leading to a stand for supporting a sample.
Figure 15:
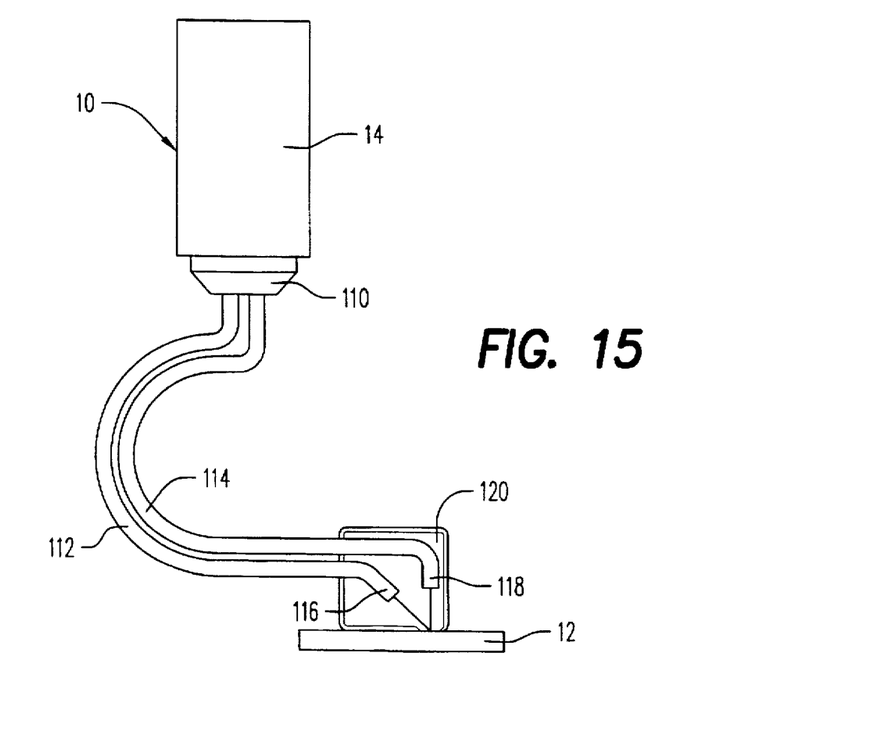
FIG. 15 is a side elevational view of the preferred embodiment of FIG. 1 with the interface module of FIG. 13 showing the two extension lines leading to a distal enclosure.

Referring to FIGS. 14 and 15, there are shown two ways to utilize the custom interface module 110 shown in FIG. 13, by way of example. The custom interface module 110 is designed for a variety of applications where other interface modules 20 could not be used, such as access to normally inaccessible areas, and is not intended to be limited the examples shown in FIGS. 14 and 15. Referring to FIG. 14, the extension lines 112, 114 of the custom interface module 110 have distal ends 116, 118 that are positioned on a stand for supporting the sample 12. Similarly, as shown in FIG. 15, the distal ends 116, 118 of the extension lines 112, 114 may be positioned within a distal enclosure 120.

It is further contemplated that the present invention may include an automatic sensing system. The automatic sensing system would automatically determine the type of interface module 20 that is attached to the color measuring device 10 and adapt the device to measure color based on the modular type. Specifically, magnetic, electro-magnetic or hall-effect switches in the lower portion 14 of the device 10 would be monitored by a computer or electrical circuit of the device to determine the type of interface module 20 installed at the lower portion. Magnets located on the upper surface of the interface module 20 would activate one or more of the switches in order to indicate to the electrical circuit the type of interface module that is attached. Since each type of interface module 20 would have a different arrangement of magnets, the type of interface module attached to the lower portion 14 of the device 10 can be automatically determined by the electrical circuit of the device. For example, the light blocking means 100 shown in FIGS. 5 through 10 may be controlled by such an automatic sensing system of the device 10.

In summary, conversion from one geometry to the other through the interchange of interface modules 20 is simple and inexpensive. Accordingly, a user could purchase a color measuring device 10 having one interface module 20, and thus one optical geometry, and also purchase interface modules having the particular optical geometries that the user needs. In addition, the user would, in effect, have a single color measuring device 10 for color measurement of samples 12 using multiple optical geometries. Further, if the user requires a custom configuration for obtaining color measurements, the user would only need to purchase a new interface module 20 instead of having to purchase an entire new color measuring device.

The present invention having been thus described with particular reference to the preferred forms thereof, it will be obvious that various changes and modifications may be made therein without departing from the spirit and scope of the invention as defined in the appended claims.

Wherefore we claim:

1. A device for measuring color of a sample, said device comprising;

means for illuminating the sample;

modular means, selected from a plurality of modular means each having a different optical geometry, optically connected to said illuminating means, for directing at least a portion of the illumination to the sample and for collecting at least a portion of a sample light reflected from the sample, said modular means having an optical geometry corresponding to that of the sample for determining the distribution of the illumination and the collection of the sample light by said modular means; and means, optically connected to said modular means, for receiving the sample light from said modular means, wherein said modular means is adapted to be optically separated from said illuminating means and said receiving means and replaced with another one of said plurality of modular means when measurement of the color of a sample having a different optical geometry is performed.

2. The device of claim 1, wherein said modular means includes a removable filter that is situated in a travel path of the illumination, and wherein said removable filter comprises a filter selected from the group consisting of: ultraviolet absorbing/visible transmitting filters, ultraviolet transmitting/visible absorbing filters, visible transmitting/infrared absorbing filters, infrared transmitting/visible blocking filters, and selective absorption filters.

3. The device of claim 1, wherein said optical geometry comprises an optical geometry selected from the group consisting of: 0/0, 0/45, 45/0, 45/45, d/0, d/8, 0/d, and 8/d.

4. The device of claim 1, wherein said optical geometry is a specular excluded sphere geometry for diffusely illuminating the sample and for directing a diffusely reflected portion of the illumination from the sample toward the said receiving means while absorbing a specularly reflected portion of the illumination from the sample as appropriate to that sample.

5. The device of claim 4, wherein said specular excluded sphere geometry includes a vertical cylinder situated about a travel path of the sample light reflected from the sample, and wherein said vertical cylinder has a highly reflectant outer surface and a highly absorbent inner surface.

6. The device of claim 1, wherein said optical geometry is a specular included sphere geometry for diffusely illuminating the sample and for directing a reflected portion of the illumination from the sample toward said receiving means, and wherein said reflected portion includes diffusely reflected illumination and specularly reflected illumination.

7. The device of claim 6, wherein said specular included sphere geometry includes a substantially planar device situated in the middle of said sphere geometry to block direct illumination of the sample.

8. The device of claim 6, wherein said specular included sphere geometry includes a substantially planar device situated in the middle of said sphere geometry to block direct illumination of the sample and a lens positioned in a travel path of the sample light reflected from the sample for directing the sample light toward said receiving means.

9. The device of claim 1, further comprising means for transmitting a reference light reflected from an interior of said modular means.

10. The device of claim 9, further comprising a blocking means situated between the sample and said transmitting means to prevent said transmitting means from receiving the reference light reflected from an interior of said modular means.

11. The device of claim 1, further comprising means for transmitting a reference light received from said illuminating means.

12. The device of claim 11, further comprising blocking means situated between said illuminating means and said means for transmitting the reference light to prevent said means for transmitting the reference light from receiving the reference light.

13. The device of claim 1, wherein said modular means includes flexible extension lines having distal ends that may be situated about the sample at a location distal to said modular means.

14. The device of claim 13, wherein said distal ends are positioned on a stand for supporting the sample.

15. The device of claim 13, wherein said distal ends are positioned within a distal enclosure.

16. The device of claim 1, further comprising sensing means for automatically determining a modular type of said modular means and for measuring the color of the sample based on said modular type.

17. The device of claim 1, further comprising means for separating the sample light into spectral components, wherein said separating means including means for producing sample signals corresponding to the levels of spectral components of the sample light.

* * * * *